United States Patent
Kubota

(10) Patent No.: US 10,603,266 B2
(45) Date of Patent: Mar. 31, 2020

(54) EYELASH CLEANING AGENT

(71) Applicant: MEDIPRODUCE, INC., Chiyoda-ku (JP)

(72) Inventor: Eri Kubota, Minato-ku (JP)

(73) Assignee: MEDIPRODUCE, INC., Tokyo (JP)

( * ) Notice: Subject to any disclaimer, the term of this patent is extended or adjusted under 35 U.S.C. 154(b) by 292 days.

(21) Appl. No.: 15/516,448

(22) PCT Filed: Oct. 9, 2015

(86) PCT No.: PCT/JP2015/078726
§ 371 (c)(1),
(2) Date: Apr. 3, 2017

(87) PCT Pub. No.: WO2016/056644
PCT Pub. Date: Apr. 14, 2016

(65) Prior Publication Data
US 2018/0221265 A1     Aug. 9, 2018

(30) Foreign Application Priority Data

Oct. 9, 2014 (JP) ................. 2014-208434

(51) Int. Cl.
| | |
|---|---|
| *A61K 8/67* | (2006.01) |
| *A61K 8/36* | (2006.01) |
| *A61Q 1/10* | (2006.01) |
| *A61Q 19/10* | (2006.01) |
| *A61K 8/97* | (2017.01) |
| *A61K 8/9711* | (2017.01) |
| *A61K 8/9789* | (2017.01) |
| *A61Q 5/02* | (2006.01) |
| *A61Q 7/00* | (2006.01) |

(52) U.S. Cl.
CPC .............. *A61K 8/67* (2013.01); *A61K 8/36* (2013.01); *A61K 8/361* (2013.01); *A61K 8/97* (2013.01); *A61K 8/9711* (2017.08); *A61K 8/9789* (2017.08); *A61Q 1/10* (2013.01); *A61Q 5/02* (2013.01); *A61Q 7/00* (2013.01); *A61Q 19/10* (2013.01)

(58) Field of Classification Search
None
See application file for complete search history.

(56) References Cited

U.S. PATENT DOCUMENTS

| | | | | |
|---|---|---|---|---|
| 5,486,509 | A * | 1/1996 | Jimenez | A61K 8/64 514/167 |
| 5,578,312 | A * | 11/1996 | Parrinello | A61K 8/0212 424/401 |
| 8,535,738 | B2 * | 9/2013 | Collins | A61K 8/347 424/735 |
| 2003/0176395 | A1 * | 9/2003 | Sakai | C08B 37/00 514/54 |
| 2006/0093566 | A1 | 5/2006 | Mizutani et al. | |
| 2010/0080766 | A1 | 4/2010 | Dumousseaux et al. | |
| 2010/0316581 | A1 * | 12/2010 | Takeoka | A61K 8/39 424/59 |
| 2011/0150805 | A1 | 6/2011 | Kergosien et al. | |

FOREIGN PATENT DOCUMENTS

| | | |
|---|---|---|
| EP | 1 234 568 A1 | 8/2002 |
| EP | 2 233 154 A1 | 9/2010 |
| JP | 6-509072 A | 10/1994 |
| JP | 8-295628 A | 11/1996 |
| JP | 2006-290767 A | 10/2006 |
| JP | 2009-114170 A | 5/2009 |
| JP | 2009-235001 A | 10/2009 |
| JP | 2013-540135 A | 10/2013 |
| JP | 2015-174854 A | 10/2015 |
| WO | 01/39731 A1 | 6/2001 |
| WO | WO 2006/097359 A1 | 9/2006 |

OTHER PUBLICATIONS

Barrett (www.quackwatch.org/01QuackeryRelatedTopics/homeo. html) accessed Jun. 6, 2017.*
International Preliminary Report on Patentability and Written Opinion dated Apr. 11, 2017 in PCT/JP2015/078726 (with English translation).
International Search Report dated Dec. 8, 2015 in PCT/JP2015/078726 filed Oct. 9, 2015.
Extended European Search Report dated Jul. 21, 2017 in Patent Application No. 15848801.5.

* cited by examiner

*Primary Examiner* — Susan Hoffman
(74) *Attorney, Agent, or Firm* — Oblon, McClelland, Maier & Neustadt, L.L.P.

(57) ABSTRACT

Provided is an eyelash cleaning agent capable of promoting an eyelash elongation effect. The eyelash cleaning agent comprising a cleaning ingredient, and further comprising a vitamin D ingredient, a hair growth ingredient, and a hair loss prevention ingredient, not only reduces a degree of obstruction of the meibomian glands, but also realizes an eyelash elongation effect. Preferably, the vitamin D is vitamin D3, the hair growth ingredient is a ginseng extract, and the hair loss prevention ingredient is *kjellmaniella gyrata* extract. Additionally, the cleaning ingredient is preferably isostearyl acid or a derivative thereof.

2 Claims, 4 Drawing Sheets

(A)

(B)

(C)

(D)

EYELASH CLEANING AGENT

FIELD OF THE INVENTION

The present invention relates to an eyelash cleaning agent. More specifically, the present invention relates to an eyelash cleaning agent capable of promoting an eyelash elongation effect.

BACKGROUND ART

Meibomian Gland Dysfunction (MGD) is currently thought to be the leading risk factor for dry eye. MGD readily occurs when the eye lacks hygienic care, and impairs the function of the meibomian glands, causing the eye to feel dry. Further, MGD causes various dry eye symptoms, such as hyperemia and a sandy feeling of foreign matter in the eye. While such symptoms readily occur in females who wear eye makeup, these symptoms also readily occur in males who do not wear makeup when the eye lacks hygienic care.

As means for keeping the meibomian glands clean, eye cleaning is recommended by doctors and the like. Cleaning the eye keeps the meibomian glands sanitary, preventing and improving chronic dry eye. Thus, effective eye cleaning has been proposed.

For example, Patent Document 1 proposes a formulation for treatment of the symptoms of dry eye. This formulation incorporates natural jojoba wax, or components thereof, to enhance the spreading of the artificial tear and eyedrop, as well as stabilize the eyedrop. The improved performance of the jojoba wax supplemented tear relieves irritation and discomfort as well as sharpens the blurred vision. This Patent Document 1 provides an ophthalmic composition that contains a wax, sperm oil, or orange roughy oil in an amount effective for lubricating the eye, the wax being selected from a group consisting of jojoba wax or a component or derivative thereof.

Patent Documents

Patent Document 1: Japanese Translation of PCT International Application No. 2007-528897

SUMMARY OF THE INVENTION

Problems to be Solved by the Invention

The present inventors conducted extensive research on eye cleaning agents having a dry eye prevention and improvement effect, and discovered that washing the eye with a particular cleaning agent not only improves Meibomian Gland Dysfunction (MGD) type dry eye, but also has a profound effect on eyelash elongation as a result of additive ingredients in the cleaning agent.

The present invention was achieved on the basis of the above-described knowledge, and therefore it is an aim of the present invention to provide an eyelash cleaning agent capable of promoting an eyelash elongation effect.

Means for Solving the Problems

The present inventors, taking into consideration the special characteristics of an eyelash cleaning agent, developed an eyelash cleaning agent capable of reducing a degree of obstruction of the meibomian glands and achieving an eyelash elongation effect, on the basis of various research.

An eyelash cleaning agent according to the present invention comprises a cleaning ingredient, and further comprises a vitamin D ingredient, a hair growth ingredient, and a hair loss prevention ingredient.

This eyelash cleaning agent is a liquid cleaning agent comprising the cleaning ingredient, and therefore is capable of effectively cleaning the eye and reducing a degree of obstruction of the meibomian glands. Further, with inclusion of vitamin D, this eyelash cleaning agent is capable of supplying hair growth ingredient and hair loss prevention ingredient to the cleaned eye and causing vitamin D to effectively act on the cleaned eye having a reduced degree of obstruction of the meibomian glands. As a result, the eyelash cleaning agent is capable of promoting eyelash enhancement (growth). Additionally, with further inclusion of the hair growth ingredient, this eyelash cleaning agent interacts with the vitamin D, making it possible to further promote eyelash enhancement (growth). Furthermore, with inclusion of the hair loss prevention ingredient, this eyelash cleaning agent is capable of causing the hair loss prevention ingredient to effectively act on the cleaned eye having a reduced degree of obstruction of the meibomian glands, and maintaining the eyelashes as healthy eyelashes.

In the eyelash cleaning agent according to the present invention, vitamin D is preferably vitamin D3. The hair growth ingredient is preferably a ginseng extract. The hair loss prevention ingredient is preferably *kjellmaniella gyrata* extract.

In the eyelash cleaning agent according to the present invention, the cleaning ingredient is preferably isostearic acid or a derivative thereof.

Effect of the Invention

According to the present invention, it is possible to provide an eyelash cleaning agent capable of promoting an eyelash elongation effect. This eyelash cleaning agent can clean root portions of the eyelashes during eyelash cleaning and reduce the degree of obstruction of the meibomian glands. As a result, this eyelash cleaning agent is capable of improving and maintaining the health of the root portions of the eyelashes, and achieving eyelash growth and hair loss prevention.

EMBODIMENTS OF THE INVENTION

Figure 1:
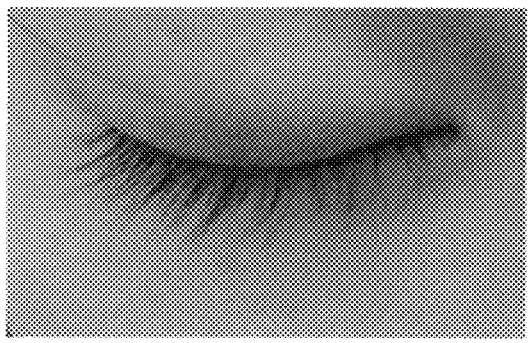
FIGS. 1A to 1D show images before use and after two months of use of an eyelash cleaning agent according to the present invention.
Figure 1:
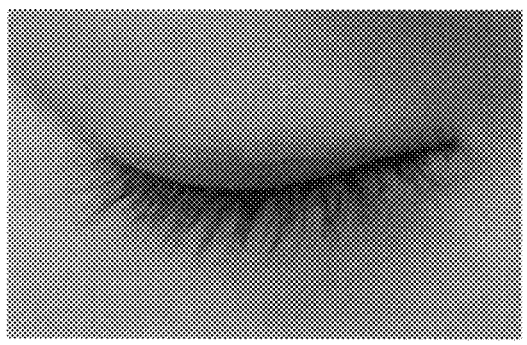
Figure 1:
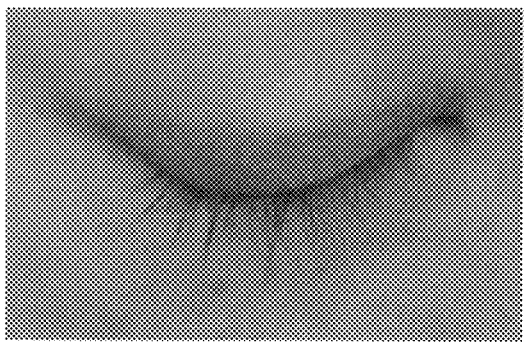
Figure 1:
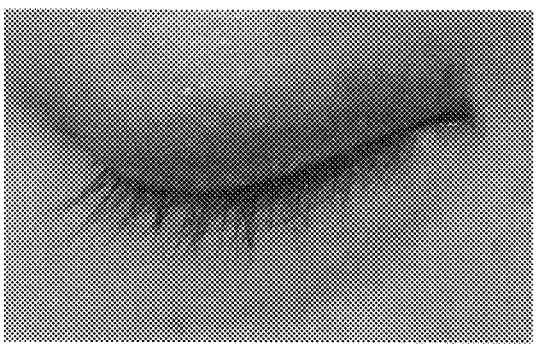

The eyelash cleaning agent according to the present invention will now be described. Note that the present invention is not limited to the following embodiment and can be modified in various ways within the scope of the gist of the present invention.

[Eyelash Cleaning Agent]

An eyelash cleaning agent according to the present invention comprises a cleaning ingredient, and further comprises a vitamin D ingredient, a hair growth ingredient, and a hair loss prevention ingredient. This eyelash cleaning agent is a liquid cleaning agent comprising the cleaning ingredient, and therefore is capable of effectively cleaning the eye and reducing a degree of obstruction of the meibomian glands. Further, with inclusion of vitamin D, this eyelash cleaning agent is capable of supplying the hair growth ingredient and the hair loss prevention ingredient to the cleaned eye and causing vitamin D to effectively act on the cleaned eye having a reduced degree of obstruction of the meibomian glands. As a result, this eyelash cleaning agent is capable of promoting eyelash enhancement (growth). Additionally, with further inclusion of the hair growth ingredient, this eyelash cleaning agent interacts with the vitamin D, making it possible to further promote eyelash enhancement (growth). Furthermore, with inclusion of the hair loss prevention ingredient, this eyelash cleaning agent is capable of causing the hair loss prevention ingredient to effectively act on the cleaned eye having a reduced degree of obstruction of the meibomian glands, and maintaining the eyelashes as healthy eyelashes.

According to the eyelash cleaning agent having such an effect, it is possible to promote an eyelash elongation effect and improve and maintain the health of the root portions of the eyelashes. As a result, this eyelash cleaning agent is capable of achieving eyelash growth and hair loss prevention.

In the following, the ingredients of the eyelash cleaning agent are described.

(Vitamin D)

Vitamin D is said to be effective in maintaining healthy vascular function, and is presumed to act as an ingredient capable of promoting eyelash enhancement (growth). Examples of the vitamin D include a vitamin D2 (ergocalciferol), a vitamin D3 (cholecalciferol), a vitamin D4, a vitamin D5, a vitamin D6, a vitamin D7, 1,25-dihydroxycholecalciferol, and the like. Among these, use of a plant-derived vitamin D2 (ergocalciferol) and an animal-derived vitamin D3 (cholecalciferol) is preferred, and use of a vitamin D3 (cholecalciferol) is particularly preferred.

Such a vitamin D (preferably the vitamin D3 in particular) is preferably contained in the eyelash cleaning agent in an amount within a range from 0.00002 wt % (0.2 ppm) to 0.002 wt % (20 ppm) inclusive. With vitamin D (vitamin D3 in particular) within this range, it is possible to cause vitamin D (vitamin D3 in particular) to act more effectively on the cleaned eye having a reduced degree of obstruction of the meibomian glands. While the vitamin D still has an effect to a certain degree as long as it is contained, even if the content is less than 0.00002 wt %, the effect may not be sufficient. On the other hand, while the vitamin D still has an effect if the content exceeds 0.002 wt %, the extent of the effect minimally changes. It should be noted that the more preferred content is within a range from 0.00002 wt % to 0.0005 wt % inclusive, which allows vitamin D (vitamin D3 in particular) to act more effectively.

(Hair Growth Ingredient)

The hair growth ingredient acts as an ingredient capable of promoting eyelash growth. Examples of the hair growth ingredient include extracts such as a ginseng extract. As the ginseng extract, Asian ginseng extract can be preferably used. Asian ginseng extract has the effect of promoting hair growth. The reason is that Asian ginseng is believed to promote blood circulation and have an anti-oxidant effect on the skin as well as a moisturizing effect on the skin and hair. Examples of ingredients other than Asian ginseng extract that promote blood circulation include placenta extract, capsaicin, garlic extract, swertia extract, argane oil, ginkgo leaf extract, watercress extract, jojoba oil, and the like. Examples of ingredients having an anti-oxidant effect on the skin include aram seeds, mulberry bark extract, proanthocyanidins, ginkgo leaf extract, wild yam, garlic extract, argane oil, jojoba oil, and the like. Examples of ingredients having a moisturizing effect include mulberry bark extract, brown alga extract, bio polyphosphoric acid, watercress extract, panthenol, jojoba oil, and the like.

Such a ginseng extract (preferably the Asian ginseng extract in particular) is preferably contained in the eyelash cleaning agent as an extract containing solvent in an amount within a range from 0.000001 wt % (0.01 ppm) to 0.0001 wt % (1 ppm) inclusive. With the ginseng extract (the Asian ginseng extract in particular) within this range, the ginseng extract interacts with the Vitamin D, making it possible to further promote eyelash enhancement (growth) in the cleaned eye having a reduced degree of obstruction of the meibomian glands. While the ginseng extract still has an effect to a certain degree as long as it is contained, even if the content is less than 0.000001 wt %, the effect may not be sufficient. On the other hand, while the ginseng extract still has an effect if the content exceeds 0.0001 wt %, the extent of the effect minimally changes. It should be noted that the more preferred content is within a range from 0.000001 wt % to 0.00005 wt % inclusive, which allows the ginseng extract (the Asian ginseng extract in particular) to act more effectively.

(Hair Loss Prevention Ingredient)

The hair loss prevention ingredient acts as an ingredient capable of preventing eyelash loss. The hair loss prevention ingredient is also effective as a moisturizing ingredient. Examples of the hair loss prevention ingredient include *kjellmaniella gyrata* extract, hinokitiol, calcium pantothenate, pentadecanoic acid glycerides, and the like. Among these, use of *kjellmaniella gyrata* extract as the hair loss prevention ingredient is preferred. This *kjellmaniella gyrata* extract contains a fucoidan as a main component. The types of fucoidan include U-fucoidan, G-fucoidan, and F-fucoidan, and each have a hair growth effect and promote tissue regeneration. In particular, the *kjellmaniella gyrata* extract composed mainly of fucoidan derived from seaweed is excellent for hair growth, and can be preferably used.

Such a *kjellmaniella gyrata* extract is preferably contained in the eyelash cleaning agent as an extract containing solvent in an amount within a range from 0.000002 wt % (0.02 ppm) to 0.0002 wt % (2 ppm) inclusive. With the *kjellmaniella gyrata* extract within this range, the *kjellmaniella gyrata* extract can effectively act on the cleaned eye having a reduced degree of obstruction of the meibomian glands, and maintain the eyelashes as healthy eyelashes. While the *kjellmaniella gyrata* extract still has an effect to a certain degree as long as it is contained, even if the content is less than 0.000002 wt %, the effect may not be sufficient. On the other hand, while the *kjellmaniella gyrata* extract still has an effect if the content exceeds 0.0002 wt %, the extent of the effect minimally changes. It should be noted that the more preferred content is within a range from 0.000002 wt % to 0.00005 wt % inclusive, which allows the *kjellmaniella gyrata* extract to act more effectively.

(Cleaning Agent)

The cleaning agent typically makes up most of the eyelash cleaning agent. The cleaning agent constituting the eyelash cleaning agent comprises water constituting at least 85 wt % of the eyelash cleaning agent, and a cleaning ingredient contained in the water. Examples of the cleaning ingredient include isostearic acid, polyglyceryl-4 lauryl ether, and the like. While various types of isostearic acid are available, preferred examples among these include isostearic acid PEG-25 glyceryl, polyglyceryl-4 lauryl ether, and the like.

This cleaning ingredient is preferably within a range of from 0.5 wt % to 5 wt % inclusive in the eyelash cleaning agent. With the cleaning ingredient within this range, it is possible to effectively clean the eye and reduce the degree of obstruction of the meibomian glands. As a result, the vitamin D, the hair growth ingredient, and the hair loss prevention ingredient can act effectively. When the content is less than 0.5 wt %, the cleaning effect may not be sufficient. On the other hand, while the cleaning ingredient still has an effect if the content exceeds 5 wt %, the extent of the effect may not change and the cleaning agent may cause the eye to sting. It should be noted that the more preferred content is within a range from 0.5 wt % to 2 wt % inclusive.

(Other Ingredients)

The eyelash cleaning agent according to the present invention may typically contain various other ingredients as well. For example, an extractant of the hair growth ingredient and the hair loss prevention ingredient may be contained along with the hair growth ingredient and the hair loss prevention ingredient. Such an extractant are various, but preferred examples include 1,3-butyl glycol (also referred to as BG). However, an extractant other than this may be contained. It should be noted that BG also acts as a liquid water-soluble ingredient having moisturizing properties capable of achieving a smooth feel, and can therefore be preferably used. Furthermore, BG is a kind of polyhydric alcohol and is highly compatible with water, resulting in the advantage of minimal irritation to the skin, and thus can be preferably used. When used as the extractant for the hair growth ingredient and the hair loss prevention ingredient, this BG is preferably within a range from 5 wt % to 15 wt % inclusive in the eyelash cleaning agent.

Further, examples of other ingredients include a silk amino acid, an amino acid blend, a ceramide blend, and the like. These ingredients may each be contained in the eyelash cleaning agent in an amount within a range of from 0.000001 wt % (0.01 ppm) to 0.00002 wt % (0.2 ppm) inclusive.

The silk amino acid is an ingredient expected to be effective in making the eyelashes healthier. Specific examples include hydrolyzed silk, glycine components thereof, taurine, and the like. Further, the amino acid blend is an ingredient expected to be effective in repairing damaged eyelashes, and is obtained by blending a plurality of types of amino acids. Examples of the blended amino acids include arginine, lysine HCl, glutamic acid, leucine, histidine HCl, serine, valine, aspartic acid Na, threonine, isoleucine, alanine, phenylalanine, proline, tyrosine, and the like. The amino acid blend is preferably obtained by blending two or more of these amino acids. Furthermore, the ceramide blend is an ingredient expected to be effective in repairing damaged eyelashes, and is obtained by blending a plurality of types of ceramides contained in eyelashes.

Examples of the eyelash cleaning agent according to the present invention include sodium chloride, xanthan gum, arginine, phenoxyethanol, dipotassium glycyrrhizinate, citric acid, sodium polyacrylate, phytic acid, glycine, taurine, silver oxide, sodium lauroyl lactylate, lysine HCl (L-lysine hydrochloride), sericin, glutamic acid, leucine, histidine HCl (L-histidine hydrochloride), valine, serine, threonine, sodium aspartate, isoleucine, alanine, allantoin, phenylalanine, ceramide NP, proline, cholesterol, ceramide AP, tyrosine, phytosphingosine, carbomer, disodium inosinate, disodium guanylate, ceramide EOP, corn oil, and the like. In the eyelash cleaning agent, one or two or more of these types can be blended. It should be noted that these ingredients are preferably contained in the eyelash cleaning agent at a desired ratio in accordance with the ingredients, and are blended within a range of about from 0.000001 wt % (0.01 ppm) to 0.7 wt % inclusive.

The ingredients of the eyelash cleaning agent can be analyzed qualitatively and quantitatively using typical analytical means for each ingredient. Examples of the analytical means include gas chromatography and liquid chromatography. These analytical means are trace component analytical means typically performed by those skilled in the art, and the analyses (qualitative and quantitative) may each be performed with the analytical conditions set as appropriate. Gas chromatography can preferably analyze vaporizable ingredient materials, and can perform highly sensitive trace analysis after conditions such as type of carrier gas, type of column, and column temperature control are set as desired. Liquid chromatography can preferably analyze ingredient materials that do not vaporize, and can perform highly sensitive trace analysis after conditions such as pressure, type of solvent, type of column, column temperature control, and type of detector are set as desired.

The content of each ingredient described above is analyzed by such gas chromatography or liquid chromatography. For example, the cleaning ingredient such as isostearic acid PEG-25 glyceryl used in test examples described later can be preferably analyzed by gas chromatography. The vitamin D ingredient such as cholecalciferol (vitamin D3) can be preferably analyzed by gas chromatography or liquid chromatography. The hair growth ingredient such as Asian ginseng extract can be preferably analyzed by liquid chromatography. The hair loss prevention ingredient such as *kjellmaniella gyrata* extract can be preferably analyzed by liquid chromatography. It should be noted that the other ingredients described above can be analyzed by gas chromatography or liquid chromatography as well. In the measurement of each ingredient, the major ingredient contained in the ingredient is detected and set to a reference value or a calibration value, or the like, making it possible to perform the respective qualitative and quantitative analyses.

(Manufacturing Method)

The eyelash cleaning agent can be manufactured by mixing each ingredient. First, weighed raw ingredients are mixed in water and subsequently heated and stirred at about 70° C. to 80° C. to dissolve the ingredients in the water and make the mixture uniform. At this time, the weighed raw ingredients may be mixed and the mixture may be made uniform after first dissolving oil-based ingredients and water-based ingredients. In this case, the oil-based ingredients and then the water-based ingredients can be dissolved, and each dissolved solution can be mixed together to make the mixture uniform. In this way, the eyelash cleaning agent can be manufactured. While the eyelash cleaning agent is manufactured by adding and mixing each ingredient in a predetermined amount, each ingredient is weighed and added so that the content of each ingredient of the manufactured eyelash cleaning agent is within the range previously described. Typically, whether or not the blending ratio and the content ratio are the same is confirmed by analysis using the gas chromatography or liquid chromatography described above. Thus, the blending ratio of each ingredient added during the manufacture of the eyelash cleaning agent is consistent with the content ratio of each ingredient contained in the manufactured eyelash cleaning agent.

(Meibomian Glands and Eyelash Growth)

Meibomian glands are organs that produce lipids. Typically 20 to 30 meibomian glands line the edge of the eye, and are related to tear evaporation and stabilization. The lipids secreted from the meibomian glands play an important role in suppressing the evaporation of tears and stabilizing tears on the surface of the eye. When secretion of the lipids fails, Meibomian Gland Dysfunction (MGD) occurs. If the meibomian glands are obstructed and do not function, eye hyperemia, dryness, and a foreign matter feel occur, and thus MGD is a leading risk factor for dry eye. In particular, many females who wear eye makeup on the edges of the eye are highly susceptible to meibomian gland obstruction, which readily causes inflammation. In addition, even in males, when the eye lacks hygienic care as a result of eye mucus, dust, pollen, dandruff, or the like, the meibomian glands are readily susceptible to obstruction, which readily causes inflammation. Further, in recent years, when the eye lacks hygienic care, the problem arises that a mite called Demodex that resides on the face lives in the pores of the eyelashes, causing inflammation, and further exacerbating the inflammation.

By cleaning the eye using the eyelash cleaning agent according to the present invention, it is possible to solve the above-described problems and eliminate blockage (reduce the degree of obstruction of the openings) of the meibomian glands. Reduction of the obstruction of the meibomian glands makes it possible to improve dry eye as well as the eyelash growth environment. Improvement of the eyelash growth environment contributes to the elongation (growth) of the eyelashes and the prevention of eyelash loss, and the significant effect is demonstrated from the test examples described later.

EXAMPLES

The present invention will now be described in further details by text examples.

[Test 1]

(Eyelash Cleaning Agent A)

An eyelash cleaning agent A of test 1 was manufactured by mixing each ingredient below. First, each weighed raw ingredient was mixed in water. Subsequently, the raw ingredients mixed in water were heated and stirred at about 75° C. to dissolve the ingredients in the water and make the mixture uniform. The ingredients of the eyelash cleaning agent A used in the test, and the corresponding contents thereof, are shown below. The remnant is water.

Isostearic acid PEG-25 glyceryl: 1 wt %
Cholecalciferol (vitamin D): 0.000025 wt %
Asian ginseng root extract: 0.000002 wt %
*Kjellmaniella gyrata* extract: 0.000004 wt %

(Test Method)

The test was conducted by a parallel-group comparison test (open test) using a total of 20 males and females between 30 and 79 years old as test subjects. Each test subject used the eyelash cleaning agent A at bedtime and at waketime for a period of two months. As for the method of use, the test subjects used the eyelash cleaning agent A after getting up and before going to bed. Among the test subjects, each female test subject washed her face as usual using normally used eye makeup remover and the like. Each male test subject and, upon washing her face, female test subject then took the eyelash cleaning agent A in hand, applied the eyelash cleaning agent A to the eye, and lightly massaged and washed away the dirt at the roots of the eyelashes.

Such a test was performed and the state of the eye, the degree of obstruction of the meibomian glands, the eyelash length, and the eyelash dirtiness were examined before use, after one month of use, and after two months of use. The results are shown in FIG. 1 to FIG. 4. FIGS. 1A and 1C show images before use, and FIGS. 1B and 1D show images after two months of use.

(Evaluation of Degree of Obstruction of Meibomian Glands)

Figure 2:
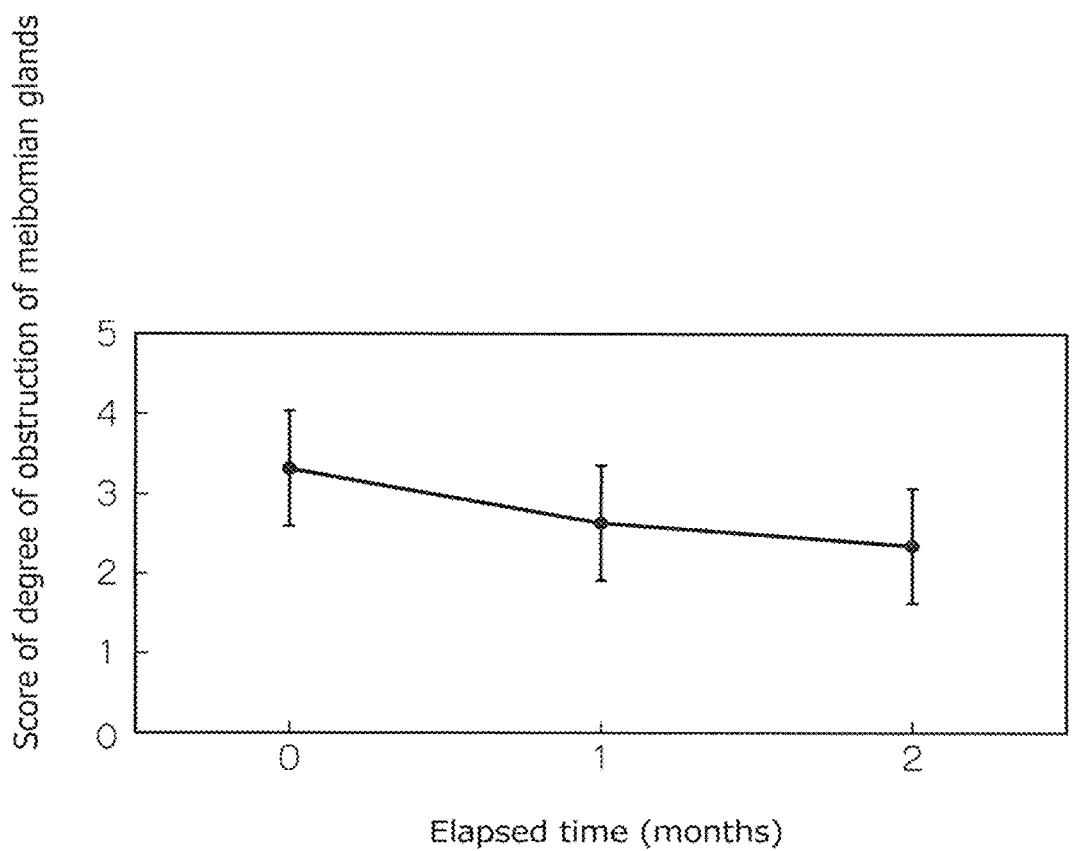
FIG. 2 is a graph showing the results of the degree of obstruction of the meibomian glands when the eyelash cleaning agent is used.

Typically, 20 to 30 meibomian glands line the edge of the eye. The degree of obstruction of the meibomian glands was evaluated using the scores below, and the results are shown in FIG. 2. The results are expressed by the range and average value of 20 persons. On day 0 before use, the average score was 3.31. After one month of use, the average score was 2.63. After two months of use, the average score was 2.31. The degree of obstruction of the meibomian glands improved over time with use.

Score of 0: No obstruction
Score of 1: 25% or less obstructed
Score of 2: More than 25% and 50% or less obstructed
Score of 3: More than 50% and 75% or less obstructed
Score 4: More than 75% obstructed (Eyelash Length)

Figure 3:
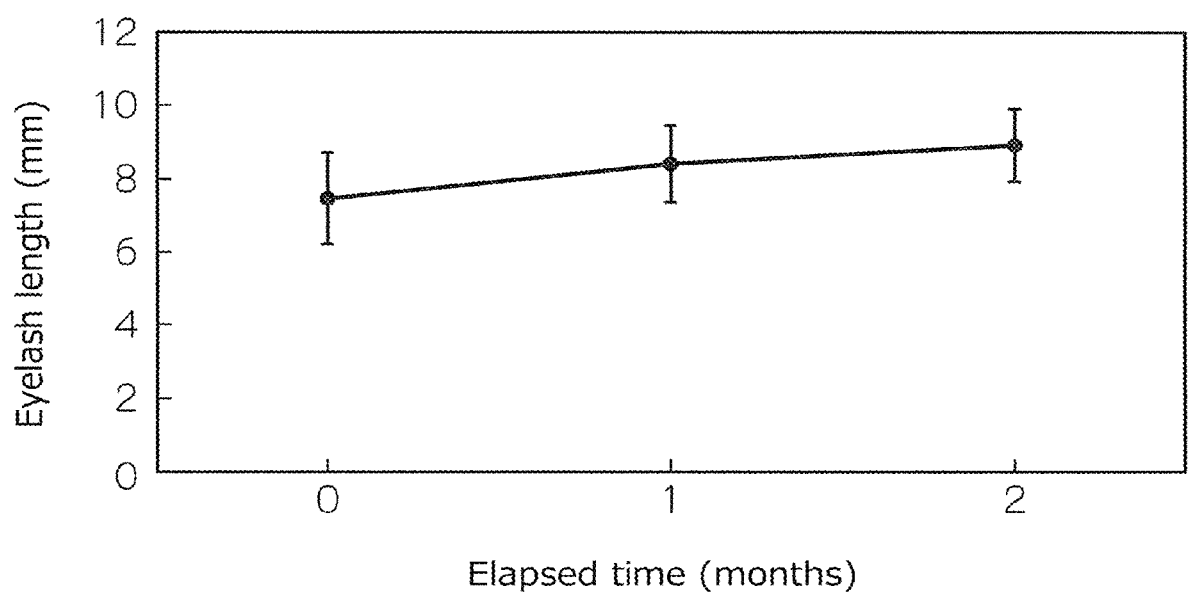
FIG. 3 is a graph showing the results of the length of the eyelashes when the eyelash cleaning agent is used.

The eyelash length was evaluated from images, and is shown in FIG. 3. The results are expressed by the range and average value of 20 persons. On day 0 before use, the average eyelash length was 7.44 mm. After one month of use, the average eyelash length was 8.38 mm. After two months of use, the average eyelash length was 8.90 mm. The eyelash length was elongated over time with use.

(Eyelash Dirtiness)

Figure 4:
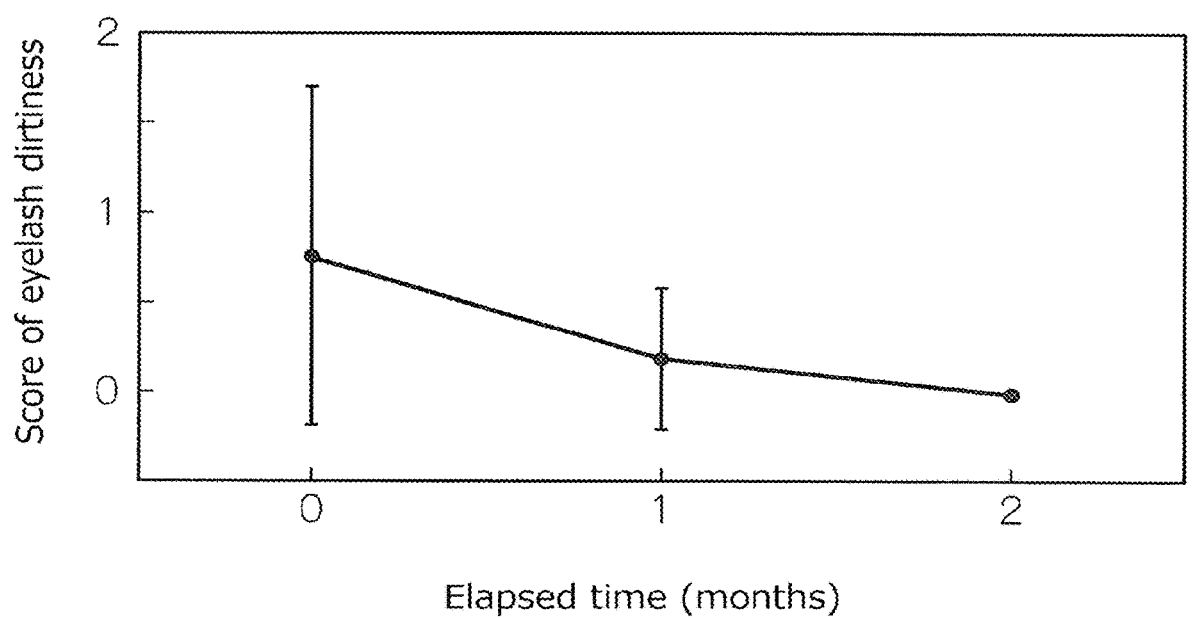
FIG. 4 is a graph showing the results of the dirtiness of the eyelashes when the eyelash cleaning agent is used.

The eyelash dirtiness was evaluated using the scores below, and is shown in FIG. 4. The results are expressed by the range and average value of 20 persons. On day 0 before use, the average score was 0.75. After one month of use, the average score was 0.19. After two months of use, the average score was 0.00. The eyelash dirtiness improved over time with use.

Score of 0: Clear
Score of 1: Just a little dirty
Score of 2: Little dirty
Score of 3: Dirty
Score of 4: Very dirty According to the above test, the test subjects experienced elimination of eye discomfort, improvement in eyelash health, elimination of meibomian gland blockage, and eyelash elongation with use of the eyelash cleaning agent A, confirming the effects of the present invention. In addition, the test subjects had no feeling of dryness, and thus a feeling of dry eye improvement was also achieved.

[Test 2 and Comparison Tests 1 to 6]

Tests were conducted using the eyelash cleaning agents of test 2 and comparison tests 1 to 6 below. The tests were conducted on the test subjects over a short period of two weeks rather than the same long period of two months as test 1, and a sensory evaluation test was conducted with regard to whether or not the same effects as test 1 were achieved. The following describes the ingredients and the sensory evaluation results of eyelash cleaning agents B to H in test 2 and comparison tests 1 to 6.

[Test 2]

The eyelash cleaning agent B of test 2 was manufactured by changing the ingredients of the eyelash cleaning agent A of test 1 to the content ratios below.

Isostearic acid PEG-25 glyceryl: 2 wt %
Cholecalciferol (vitamin D): 0.00025 wt %
Asian ginseng root extract: 0.00002 wt %
*Kjellmaniella gyrata* extract: 0.00004 wt %

(Comparison Test 1)

The eyelash cleaning agent C of comparison test 1 was manufactured by changing the ingredients of the eyelash cleaning agent A of test 1 as indicated below. This eyelash cleaning agent C does not contain vitamin D.

Isostearic acid PEG-25 glyceryl: 1 wt %
Asian ginseng root extract: 0.000002 wt %
*Kjellmaniella gyrata* extract: 0.000004 wt %

(Comparison Test 2)

The eyelash cleaning agent D of comparison test 2 was manufactured by changing the ingredients of the eyelash cleaning agent A of test 1 as indicated below. This eyelash cleaning agent D does not contain Asian ginseng root extract.

Isostearic acid PEG-25 glyceryl: 1 wt %
Cholecalciferol (vitamin D): 0.000025 wt %
*Kjellmaniella gyrata* extract: 0.000004 wt %

(Comparison Test 3)

The eyelash cleaning agent E of comparison test 3 was manufactured by changing the ingredients of the eyelash cleaning agent A of test 1 as indicated below. This eyelash cleaning agent E does not contain *kjellmaniella gyrata* extract.

Isostearic acid PEG-25 glyceryl: 1 wt %
Cholecalciferol (vitamin D): 0.000025 wt %
Asian ginseng root extract: 0.000002 wt %

(Comparison Test 4)

The eyelash cleaning agent F of comparison test 4 was manufactured by changing the ingredients of the eyelash cleaning agent A of test 1 as indicated below. This eyelash cleaning agent F does not contain vitamin D or Asian ginseng extract.

Isostearic acid PEG-25 glyceryl: 1 wt %
*Kjellmaniella gyrata* extract: 0.000004 wt %

(Comparison Test 5)

The eyelash cleaning agent G of comparison test 5 was manufactured by changing the ingredients of the eyelash cleaning agent A of test 1 as indicated below. This eyelash cleaning agent G does not contain vitamin D or *kjellmaniella gyrata* extract.

Isostearic acid PEG-25 glyceryl: 1 wt %
Asian ginseng root extract: 0.000002 wt %

(Comparison Test 6)

The eyelash cleaning agent H of comparison test 6 was manufactured by changing the ingredients of the eyelash cleaning agent A of test 1 as indicated below. This eyelash cleaning agent H does not contain Asian ginseng extract or *kjellmaniella gyrata* extract.

Isostearic acid PEG-25 glyceryl: 1 wt %
Cholecalciferol (vitamin D): 0.000025 wt %

(Sensory Evaluation Test)

The eyelash cleaning agents B to H of test 2 and comparison tests 1 to 6 were each used for two weeks on two male test subjects. The tests were performed using the same method of use as test 1. Specifically, the test subjects washed their faces as usual at bedtime and at waketime and then took the eyelash cleaning agent in hand, applied the eyelash cleaning agent to the eye, and lightly massaged and washed away the dirt at the roots of the eyelashes, for two weeks.

(Sensory Evaluation Results)

As a sensory evaluation, the test subjects were interviewed, and a sensory evaluation of discomfort and the like was conducted. In addition, the eyelash length of each test subject was measured.

According to the interview-based sensory evaluation, all test subjects found that "eye discomfort was eliminated and the hygienic feel of the eyelashes improved" for each of the eyelash cleaning agents B to H in the same way as during use of the eyelash cleaning agent A. Further, all test subjects found that "the eyelash cleaning agent did not sting the eye" for each of the eyelash cleaning agents B to H. This infers that, in the eyelash cleaning agents B to H that contain a cleaning ingredient, the cleaning ingredient acts effectively and the degree of obstruction of the meibomian glands is improved in the same way as test 1.

Further, the test subjects found that, for the eyelash cleaning agents B, C, D, and F that contain *kjellmaniella gyrata* extract, which has a moisturizing effect, "there was no feeling of dryness and the dry eye improved."

With regard to eyelash elongation, even though the test period was two weeks, elongation of about 1 mm was confirmed with the eyelash cleaning agents B and E that contain vitamin D and Asian ginseng extract. However, for the eyelash cleaning agents C, D, F, G, and H that do not contain vitamin D or Asian ginseng extracts, clear elongation was not confirmed.

From the above test results, the effects and ranges of content of the cleaning ingredient, the vitamin D, the hair growth ingredient, and the hair loss ingredient set forth in the "Embodiments of the Invention" section were demonstrated. In particular, in the specific tests A and B that used the eyelash cleaning agents A and B, the isostearic acid PEG-25 glyceryl serving as the cleaning ingredient was confirmed to have an effect in the present invention in an amount within the range from 1 wt % to 2 wt % inclusive. The cholecalciferol serving as the vitamin D was confirmed to have an effect in the present invention in an amount within the range from 0.000025 wt % to 0.00025 wt % inclusive. The Asian ginseng root extract serving as the hair growth ingredient was confirmed to have an effect in the present invention in an amount within the range from 0.000002 wt % to 0.00002 wt % inclusive. The *kjellmaniella gyrata* extract serving as the hair loss prevention ingredient was confirmed to have an effect in the present invention in an amount within the range from 0.000004 wt % to 0.00004 wt % inclusive.

What is claimed is:

1. An eyelash cleaning agent, comprising a cleaning ingredient, and further comprising a vitamin D ingredient, a hair growth ingredient, and a hair loss prevention ingredient,
    wherein the cleaning ingredient comprises from 1 wt % to 2 wt % of isostearic acid or a derivative thereof,
    wherein the vitamin D is a vitamin D3 comprised in an amount of from 0.000025 wt % to 0.00025 wt %,
    wherein the hair growth ingredient is an asian ginseng extract comprised in an amount of from 0.000002 wt % to 0.00002 wt %,
    wherein the hair loss prevention ingredient is a *kjellmaniella gyrata* extract comprised in an amount of from 0.000004 wt % to 0.00004 wt %,
    wherein the wt. % of each of the cleaning ingredient, the vitamin D ingredient, the hair growth ingredient, and the hair loss prevention ingredient is based on a total amount of the eyelash cleaning agent,
    wherein the asian ginseng extract and the *kjellmaniella gyrata* extract comprise a solvent, and
    wherein the solvent is 1,3-butyl glycol.

2. The eyelash cleaning agent according to claim 1, wherein the isostearic acid or the derivative thereof is isostearic acid PEG-25 glyceryl.

* * * * *